(12) United States Patent
Lal

(10) Patent No.: US 10,098,532 B2
(45) Date of Patent: Oct. 16, 2018

(54) SYSTEMS, METHODS AND APPARATUS FOR TRACKING CHANGES IN AN OCULAR SCENE

(71) Applicant: Rakesh Mohan Lal, Cambridge, MA (US)

(72) Inventor: Rakesh Mohan Lal, Cambridge, MA (US)

(73) Assignee: Rakesh Lal, Lexington, MA (US)

( * ) Notice: Subject to any disclaimer, the term of this patent is extended or adjusted under 35 U.S.C. 154(b) by 214 days.

(21) Appl. No.: 15/245,138

(22) Filed: Aug. 23, 2016

(65) Prior Publication Data
US 2017/0055820 A1 Mar. 2, 2017

Related U.S. Application Data

(60) Provisional application No. 62/209,992, filed on Aug. 26, 2015.

(51) Int. Cl.
| | |
|---|---|
| *A61B 3/14* | (2006.01) |
| *A61B 3/00* | (2006.01) |
| *G02B 15/14* | (2006.01) |
| *A61B 5/00* | (2006.01) |
| *G02B 7/10* | (2006.01) |

(52) U.S. Cl.
CPC .......... *A61B 3/0025* (2013.01); *A61B 3/0041* (2013.01); *A61B 3/14* (2013.01); *A61B 5/0013* (2013.01); *A61B 5/0022* (2013.01); *G02B 7/102* (2013.01); *G02B 15/14* (2013.01); *A61B 2560/0233* (2013.01)

(58) Field of Classification Search
CPC .... A61B 3/14; A61B 1/05; A61B 3/12; A61B 1/0005; A61B 3/13
USPC ................................. 351/221, 246, 206, 205
See application file for complete search history.

(56) References Cited

U.S. PATENT DOCUMENTS 5,861,940 A * 1/1999 Robinson ............... A61B 3/113
351/205

* cited by examiner

*Primary Examiner* — Hung Dang

(57) ABSTRACT

Systems, methods and apparatus are provided through which in some aspects an ocular scene is imaged and changes in the ocular scene relative to a calibration image, are tracked. In one aspect, an imaging instrument includes an eyepiece, a light source operable to project light, an imaging system operable to image an ocular scene; and a processing system operable to receive a set of calibration images, and further operable to capture an image of the imaged ocular scene associated with a calibration image. In another aspect, a method to track changes in an ocular scene includes receiving a set of calibration images, receiving a set of landmarks on each calibration image, capturing a set of images of an ocular scene, associating each captured image with a calibration image, and detecting landmarks on each captured image wherein each detected landmark corresponds to a landmark on the associated calibration image.

20 Claims, 8 Drawing Sheets

SYSTEMS, METHODS AND APPARATUS FOR TRACKING CHANGES IN AN OCULAR SCENE

FIELD OF THE INVENTION

This application claims the benefit of U.S. Provisional Application Ser. No. 62/209,992, filed Aug. 26, 2015 under 35 U.S.C 119(e).

This invention relates generally to systems, methods and apparatus for imaging an ocular scene such as the retina, posterior chamber of the eye, anterior chamber of the eye, lens, cornea and regions surrounding the eye such as the lid and orbital, and more particularly to imaging an ocular scene and specified landmarks on the ocular scene, using an imaging instrument that receives a calibration image and identified landmarks on the calibration image.

BACKGROUND OF THE INVENTION

Diseases of the eye are the leading cause of blindness in the world today. Many diseases affect different parts of the eye, and are diagnosed by imaging and inspecting images of different parts of the eye. These parts of the eye may include the retina, the posterior segment, the lens, the anterior segment, the cornea, the sclera, or external aspects of the eye such as the eyelid and orbital. Examples of diseases that affect the eye include conditions such as retinal detachment, retinopathy caused by diabetes, hypertension or other condition, glaucoma, cataract, abrasions and lacerations of the cornea or sclera.

Many of these conditions do not present significant symptoms, and diagnosis of eye conditions such as those listed above typically occurs at a physician's or optometrist's office during the course of a routine checkup. The eye is usually examined with an ophthalmoscope or other imaging equipment, and trained physicians or optometrists usually make a diagnosis without any context of how the subject's eye has changed over time. In some cases, computer aided diagnosis (CAD) software may be used to analyze images and provide assistance to the physician, but usually these algorithms do not utilize prior history or other images of the subject's eye.

Individuals, including those at risk for such conditions, usually receive such routine checkups from their physician or optometrist every 6 months to 2 years. As a result, it may be possible for diseases of the eye to develop and go undiagnosed for years, at which point, they may be more expensive to treat or may have reached an advanced state resulting in a worse prognosis.

For the reasons stated above, and for other reasons stated below which will become apparent to those skilled in the art upon reading and understanding the present specification, there is a need in the art for a system to capture images an ocular scene repeatedly and conveniently in a home environment, using a calibration image taken by a trained physician. There is also a need to track changes in the images of the ocular scene relative to calibration images of the ocular scene, taken by a trained physician, and in particular to track changes in the images of the ocular scene at particular landmarks corresponding to physician specified landmarks in the associated calibration image.

BRIEF DESCRIPTION OF THE INVENTION

The above-mentioned shortcomings, disadvantages and problems are addressed herein, which will be understood by reading and studying the following specification.

In one aspect, an imaging instrument includes an eyepiece, a light source operable to project light through the eyepiece, an imaging system operable to image an ocular scene through the eyepiece; and a processing system operable to receive a set of one or more calibration images, and further operable to capture an image of the imaged ocular scene associated with a calibration image in the set of calibration images.

In another aspect, a system for imaging an ocular scene includes a set of machine readable instructions embodied in a non-transitory medium operable to receive a set of calibration images, further operable to receive a set of landmarks on each of the calibration images, and further operable to receive a set of captured images of an ocular scene from an imaging instrument, wherein each captured image is associated with a calibration image in the set of calibration images, and further operable to detect landmarks on each of the captured images wherein each detected landmark corresponds to a landmark in the set of landmarks on the associated calibration image.

In yet another aspect, a method to track changes in an ocular scene includes receiving a set of calibration images, receiving a set of landmarks on each calibration image, capturing a set of images of an ocular scene, associating each captured image with a calibration image in the set of calibration images, and detecting landmarks on each captured image wherein each detected landmark corresponds to a landmark on the associated calibration image.

Apparatus, systems, and methods of varying scope are described herein. In addition to the aspects and advantages described in this summary, further aspects and advantages will become apparent by reference to the drawings and by reading the detailed description that follows.

DETAILED DESCRIPTION OF THE INVENTION

In the following detailed description, reference is made to the accompanying drawings that form a part hereof, and in which is shown by way of illustration specific aspects which may be practiced. These aspects are described in sufficient detail to enable those skilled in the art to practice the aspects, and it is to be understood that other aspects may be utilized and that logical, mechanical, electrical and other changes may be made without departing from the scope of the aspects. The following detailed description is, therefore, not to be taken in a limiting sense.

The detailed description is divided into four sections. In the first section, a system level overview is described. In the second section, apparatus of aspects are described. In the third section, aspects of methods are described. Finally, in the fourth section, a conclusion of the detailed description is provided.

System Level Overview

Figure 1:
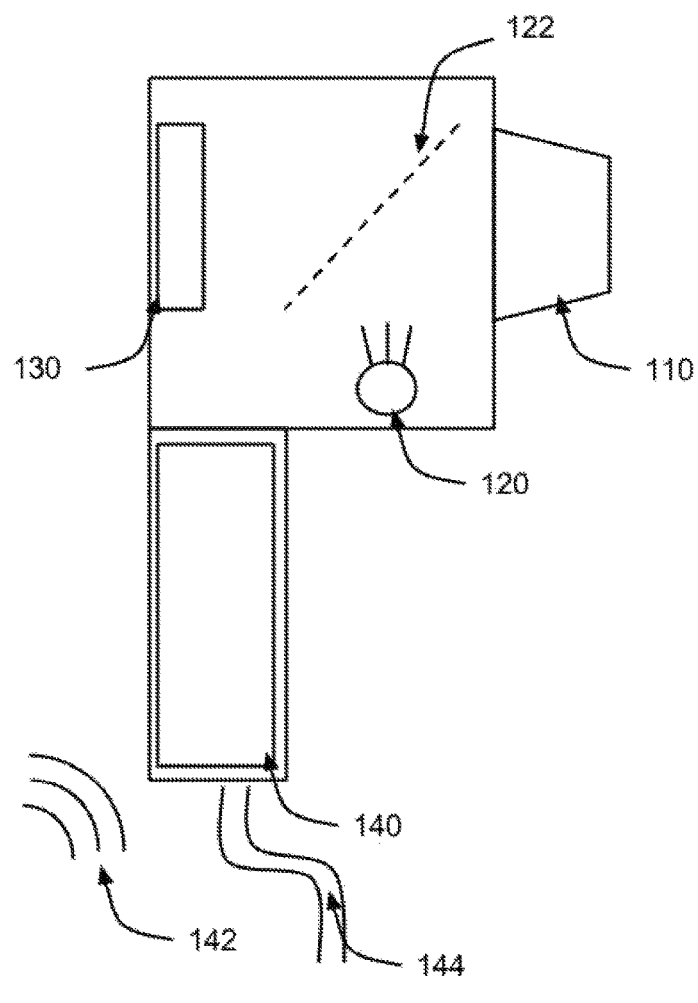
FIG. 1 is a block diagram illustrating a system to track changes in an ocular scene.

FIG. 1 is a block diagram illustrating a system track changes in an ocular scene such as the retina, posterior chamber of the eye, anterior chamber of the eye, lens, or external feature such as the eyelid or orbital. System 100 solves the need in the art to monitor and track changes in the ocular scene relative to a set of calibration images.

System 100 includes an eyepiece 110, a light source 120 operable to project light through the eyepiece, an imaging system 130 operable to image an ocular scene through the eyepiece, and a processing system 140 operable to receive a set of one or more calibration images, and further operable to capture and store an image of the imaged ocular scene associated with a calibration image in the set of calibration images. In one aspect, system 100 also includes a partial reflecting surface 122 operable to reflect light from the light source 120, such that the light is projected through the eyepiece 110. In another aspect the processing system 140 receives the set of one or more calibration images through a wireless signal 142. In another aspect the processing system 140 receives the set of one or more calibration images via a wired connection 144, using standard data transmission protocols.

Component 120 solves the need in the art to provide sufficient lighting during the process of acquiring image data used in tracking changes associated with an ocular scene.

Component 130 solves the need in the art to image an ocular scene, sufficiently illuminated by the light source.

Component 140 solves the need in the art to receive a set of one or more calibration images, and to capture an image of the ocular scene, and to further associate the captured image with an image in the received set of one or more calibration images.

The system level overview of the operation of an aspect is described in this section of the detailed description. The light source provides lighting to the ocular scene being imaged, and in one aspect projects light through the eyepiece with the aid of a partially reflecting surface onto the ocular scene.

The processing system receives a set of one or more calibration images of the ocular scene, taken at a different point in time. This set of one or more calibration images may be received through a wireless signal, or via a wired connection using standard data transmission protocols, such as Transmission Control Protocol/Internet Protocol (TCP/IP), or Universal Serial Bus (USB).

The imaging system images the ocular scene over time, including the light from the illumination system. In one aspect, the processing system sets various parameters associated with the imaging system to image the ocular scene in a particular manner based on the parameters set by the processing scene. In another aspect, the imaging system transmits a digitized representation of the ocular scene to the processing system as a stream of data.

The processing system processes the digitized representation of the ocular scene transmitted as a stream of data, and is operable to capture an image of the ocular scene. The processing system is operable to associate the captured image with a calibration image in the received set of one or more calibration images. In one aspect, the processing system includes a processor, a memory element, and a non-transitory computer readable medium operable to store instructions to process the digitized representation of the ocular scene transmitted as a stream of data, and to further capture an image of the ocular scene, and to further associate the captured image with a calibration image in the received set of one or more calibration images.

While the system 100 is not limited to any particular light source, imaging system and processing system, for sake of clarity a simplified light source, imaging system and processing system are described.

Apparatus Aspects

In the previous section, a system level overview of the operation of an aspect was described. In this section, the particular apparatus of such an aspect are described by reference to a series of diagrams.

Figure 2:
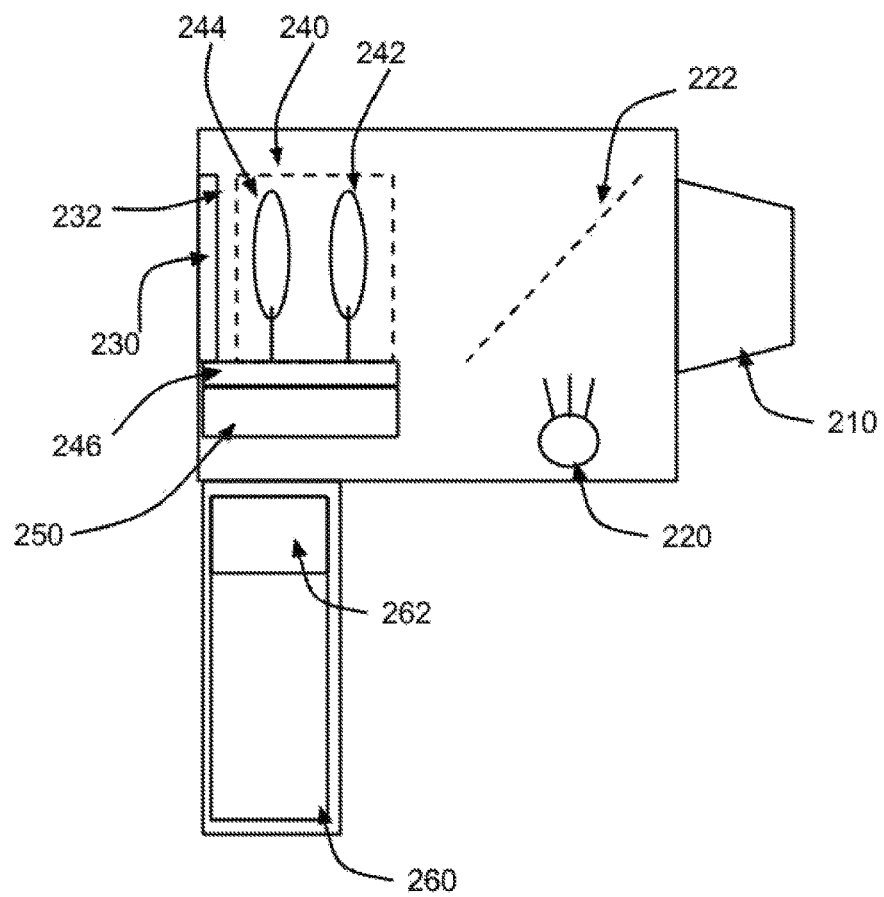
FIG. 2 is a cross section block diagram of an apparatus according to an aspect to track changes in an ocular scene by determining and using focus, magnification and orientation parameters.

FIG. 2 is a cross section block diagram of apparatus 200 according to an aspect to track changes in an ocular scene. Apparatus 200 solves the need in the art to actuate a lens system and a positioning system to capture images of an ocular scene based on asset of calibration images.

Apparatus 200 includes an eyepiece 210, a light source 220 operable to project light through the eyepiece, an imaging system 230 an imaging system operable to image an ocular scene through the eyepiece, a lens system 240 situated between the imaging system and the ocular scene, operable to focus and magnify the imaged ocular scene onto the sensor based on a focus parameter and a magnification parameter, and a processing system 260 operable to receive a set of one or more calibration images, and further operable to capture and store an image of the imaged ocular scene associated with a calibration image in the set of calibration images.

In one aspect, the imaging system 230 includes a sensor 232 operable to image an ocular scene, and is further operable to transfer the imaged ocular scene to the processing system. In another aspect, the lens system 240 includes a first lens 242, a second lens 244 situated between the first lens and the sensor, and a mechanism 246 operable to vary the distance between the first lens and second lens, and further operable to vary the distance between the second lens and the sensor based on the focus parameter and the magnification parameter. In yet another aspect, the mechanism 246 includes a motorized system operable to vary the distance between the first lens and second lens.

In one aspect, apparatus 200 also includes a partial reflecting surface 222 operable to reflect light from the light source 220, such that the light is projected through the eyepiece 210.

In one aspect, apparatus 200 also includes a positioning system 250 operable to rigidly change the orientation of the imaging and lens systems relative to the eyepiece based on an orientation parameter. In another aspect, the positioning system is operable to rigidly change the pitch, yaw, and roll orientations of the imaging and lens systems relative to the eyepiece.

In one aspect, the processing system 260 also includes a control system 262 operable to set the values of the focus parameter and the magnification parameter of the lens system based on the set of calibration images and the imaged ocular scene, and further operable to set the value of the orientation parameter of the positioning system based on the set of calibration images and the imaged ocular scene.

Figure 3:
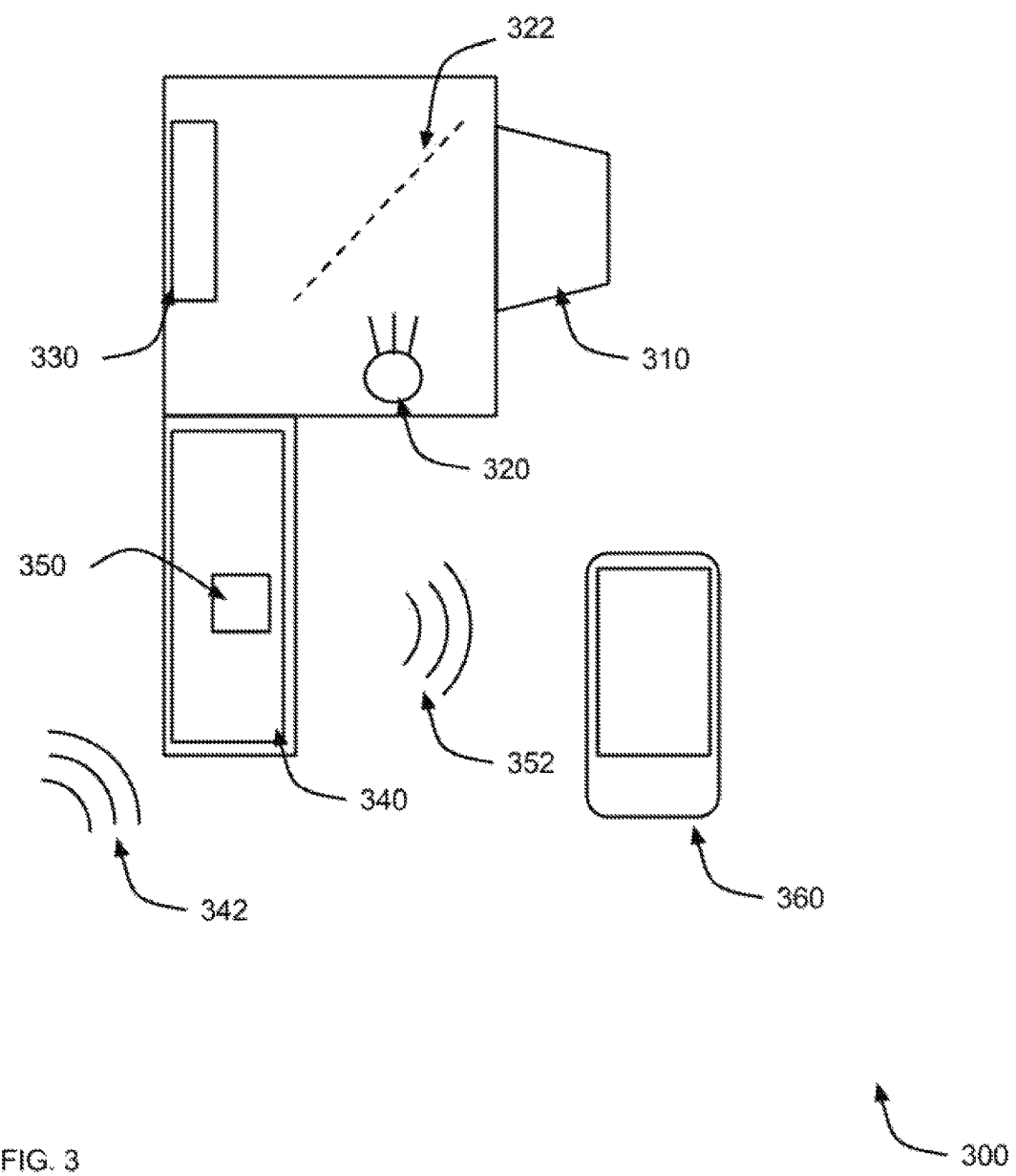
FIG. 3 is a cross section block diagram of an apparatus according to an aspect to track changes in an ocular scene by transmitting captured images to a mobile device.

FIG. 3 is a cross section block diagram of apparatus 300 according to an aspect to track the changes in an ocular scene and transmit captured images to a mobile device.

Apparatus 300 includes an eyepiece 310, a light source 320 operable to project light through the eyepiece, an imaging system 330 operable to image an ocular scene through the eyepiece, and a processing system 440 operable to receive a set of one or more calibration images, and further operable to capture and store an image of the imaged ocular scene associated with a calibration image in the set of calibration images. In one aspect, apparatus 300 also includes a partial reflecting surface 322 operable to reflect light from the light source 320, such that the light is projected through the eyepiece 310. In another aspect the processing system 340 receives the set of one or more calibration images through a wireless signal 342.

In one aspect, the processing system includes a transceiver 350 operable to transmit a set of captured images to a mobile device 360. In another aspect, the mobile device is one from the set of a smartwatch, a mobile phone, a mobile tablet, a laptop, a desktop computer, and a server. In another aspect the transceiver 350 transmits the set of captured images to the mobile device through a wireless signal 352.

Figure 4:
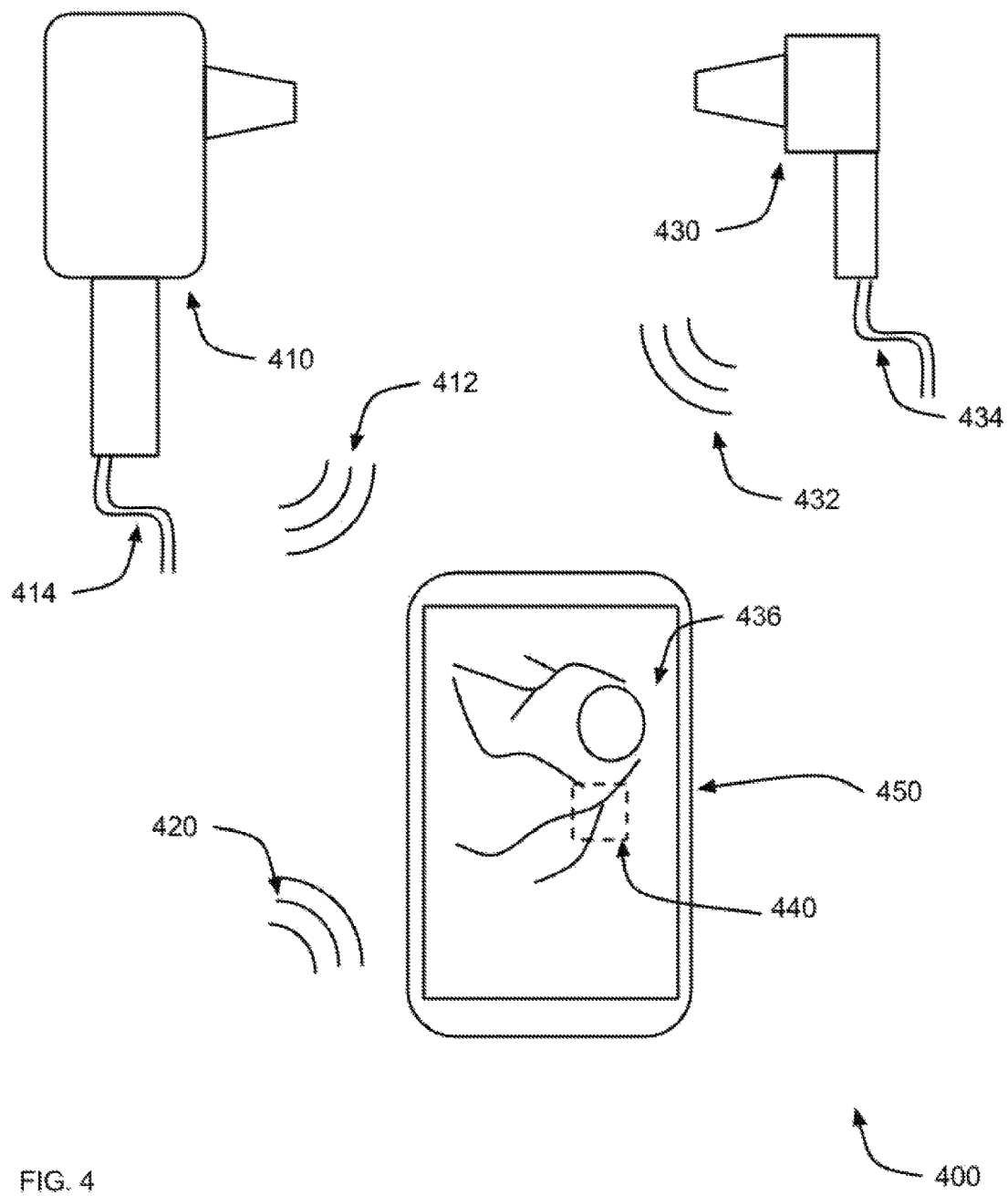
FIG. 4 is a cross section block diagram of an apparatus according to an aspect to track changes in an ocular scene by detecting landmarks in captured images received from an imaging instrument corresponding to landmarks in associated calibration images, received from a different imaging instrument.

FIG. 4 is a cross section block diagram of apparatus 400 according to an aspect to image an ocular scene. In one aspect, apparatus 400 includes a set of machine readable instructions embodied in a non-transitory medium operable to receive a set of calibration images from a first imaging instrument 410, further operable to receive a set of landmarks on each of the calibration images, and further operable to receive a set of captured images of an ocular scene from a second imaging instrument 430, wherein each captured image is associated with a calibration image in the set of calibration images, and further operable to detect landmarks 440 on each of the captured images wherein each detected landmark corresponds to a landmark in the set of landmarks on the associated calibration image. In some aspects the set of machine readable instructions are executed on a mobile device 450. In some aspects, a mobile device includes a smartwatch, a mobile phone, a mobile tablet, a computer, or a server.

In some aspects the set of calibration images may be received via a wireless signal 412, and in other aspects the set of calibration images may be received via a wired connection 414 using standard data transmission protocols, such as Transmission Control Protocol/Internet Protocol (TCP/IP), or Universal Serial Bus (USB).

In some aspects, the set of landmarks on each calibration image may be received via a wireless signal 420.

In some aspects the set of captured images may be received via a wireless signal 432, and in other aspects the set of calibration images may be received via a wired connection 434 using standard data transmission protocols, such as Transmission Control Protocol/Internet Protocol (TCP/IP), or Universal Serial Bus (USB). In some aspects, the set of machine readable instructions is operable to display the captured images 436 on the mobile device.

Figure 5:
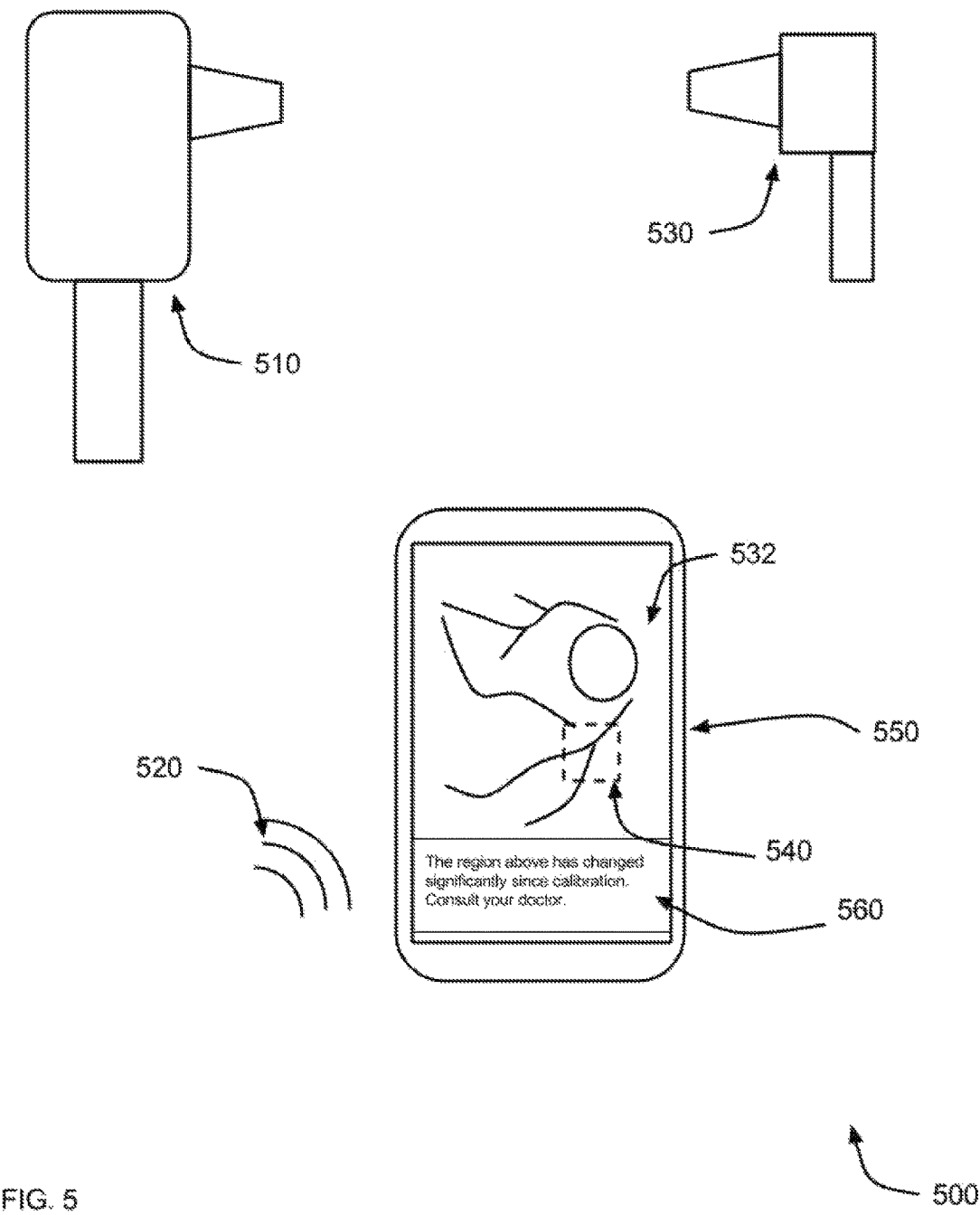
FIG. 5 is a cross section block diagram of an apparatus according to an aspect to track changes in an ocular scene by detecting landmarks in captured images received from an imaging instrument corresponding to landmarks in associated calibration images, received from a different imaging instrument, and issuing a notification if the degree of difference between the corresponding landmarks exceeds a preset threshold.

FIG. 5 is a cross section block diagram of apparatus 500 according to an aspect to image an ocular scene. In one aspect, apparatus 500 includes a set of machine readable instructions embodied in a non-transitory medium operable to receive a set of calibration images from a first imaging instrument 510, further operable to receive a set of landmarks on each of the calibration images, and further operable to receive a set of captured images of an ocular scene from a second imaging instrument 530, wherein each captured image is associated with a calibration image in the set of calibration images, and further operable to detect landmarks 540 on each of the captured images wherein each detected landmark corresponds to a landmark in the set of landmarks on the associated calibration image. In some aspects the set of machine readable instructions are executed on a mobile device 550. In some aspects, a mobile device includes a smartwatch, a mobile phone, a mobile tablet, a computer, or a server. In some aspects, the set of landmarks on each calibration image may be received via a wireless signal 520. In other aspects, the set of machine readable instructions is operable to display the captured images 436 on the mobile device.

In some aspects, the set of machine readable instructions includes a second set of machine readable instructions embodied in a non-transitory medium operable to determine the degree of change between the detected landmarks and the corresponding landmarks on the associated calibration images, and further operable to display a notification 560 if the degree of change exceeds a preset threshold.

In the machine readable instructions further includes a second set of machine readable instructions embodied in a non-transitory medium operable to determine a modified landmark associated with each landmark on each calibration image, and a third set of machine readable instructions embodied in a non-transitory medium operable to determine the degree of change between the detected landmarks and the modified landmarks associated with the corresponding landmarks on the associated calibration images, and further operable to display a notification if the degree of change exceeds a preset threshold.

In other aspects the second set of machine readable instructions includes a fourth set of machine readable instructions embodied in a non-transitory medium operable to determine a modified landmark associated with each landmark on each calibration image based on a user selected change trajectory. In some aspects, the user selected change trajectory specifies how each landmark on each calibration image changes over time. In other aspects, the user selected change trajectory is based on a set of factors including the age or health of a patient whose ocular scene is being imaged, the type of pathology found in the ocular scene, or other medical conditions associated with the patient whose ocular scene is being imaged.

Method Aspects

In the previous section, apparatus of the operation of an aspect was described. In this section, the particular methods performed by usage of such an aspect are described by reference to a series of flowcharts.

Figure 6:
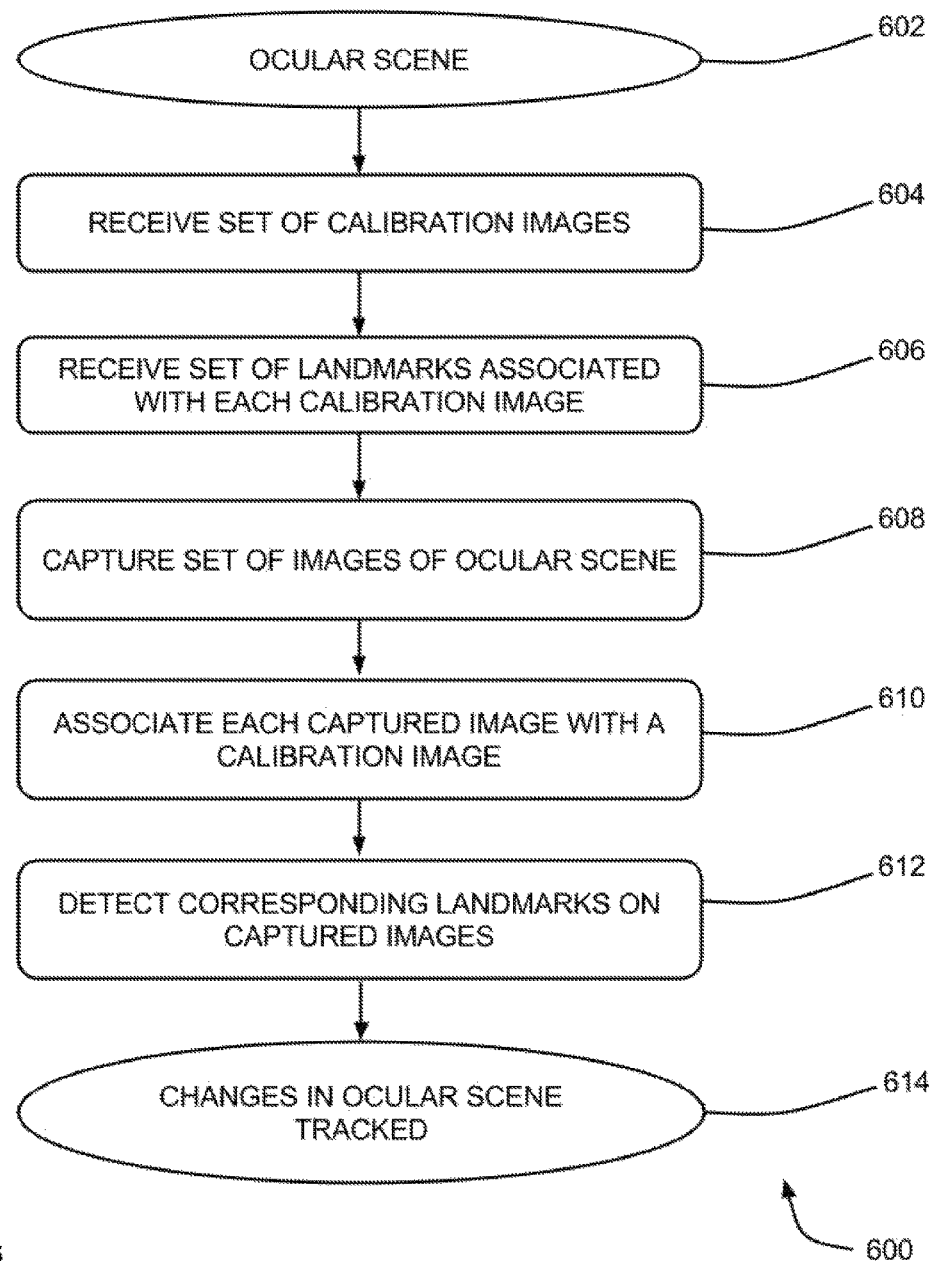
FIG. 6 is a flowchart of a method to track changes in an ocular scene.

FIG. 6 is a flowchart of method 600 to track the changes in an ocular scene. Method 600 solves the need in the art to track changes in an ocular scene over time, based on a set of calibration images and landmarks on the calibration images.

Method 600 includes an ocular scene being imaged 602, receiving a set of calibration images 604, receiving a set of landmarks on each calibration image 606, capturing a set of images of an ocular scene 608, associating each captured image with a calibration image in the set of calibration images 610, and detecting landmarks on each captured image wherein each detected landmark 612 corresponds to a landmark on the associated calibration image, and using this information to track changes in the ocular scene 614.

Figure 7:
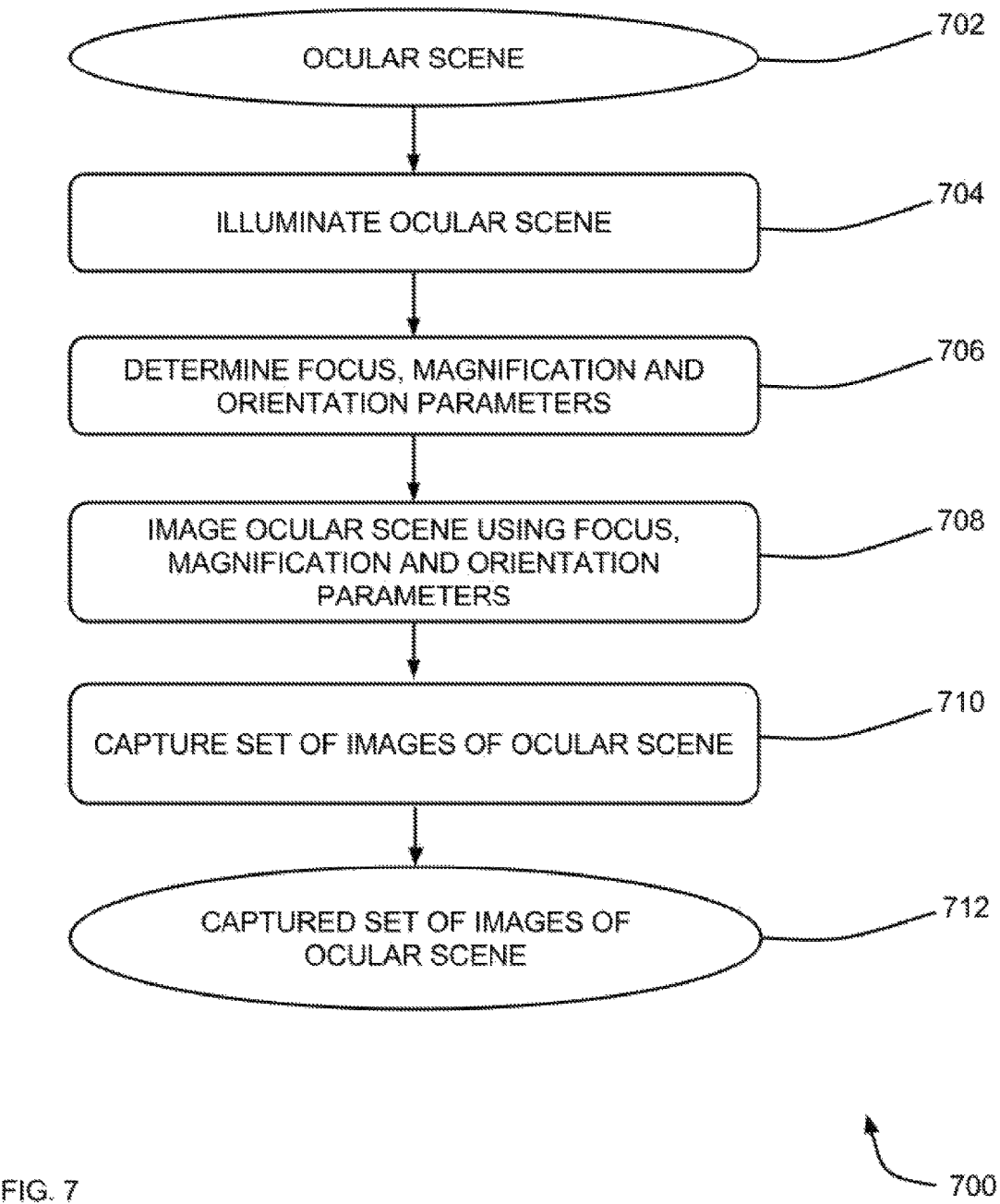
FIG. 7 is a flowchart of a method to track changes in an ocular scene by illuminating the ocular scene, and determining and using focus, magnification and orientation parameters.

FIG. 7 is a flowchart of method 700 to capture a set of images of an ocular scene. Method 700 solves the need in the art to capture images of an ocular scene using a set of calibration images by determining a set of imaging parameters with which to capture the ocular scene.

Method 700 includes an ocular scene being imaged 702, illuminating the ocular scene 704, determining focus, magnification and orientation parameters 706, based on the ocular scene and the set of received calibration images, imaging the ocular scene using the determined focus, magnification and orientation parameters 708, capturing a set of images of the ocular scene 710, resulting in a captured set of images of the ocular scene 712.

Figure 8:
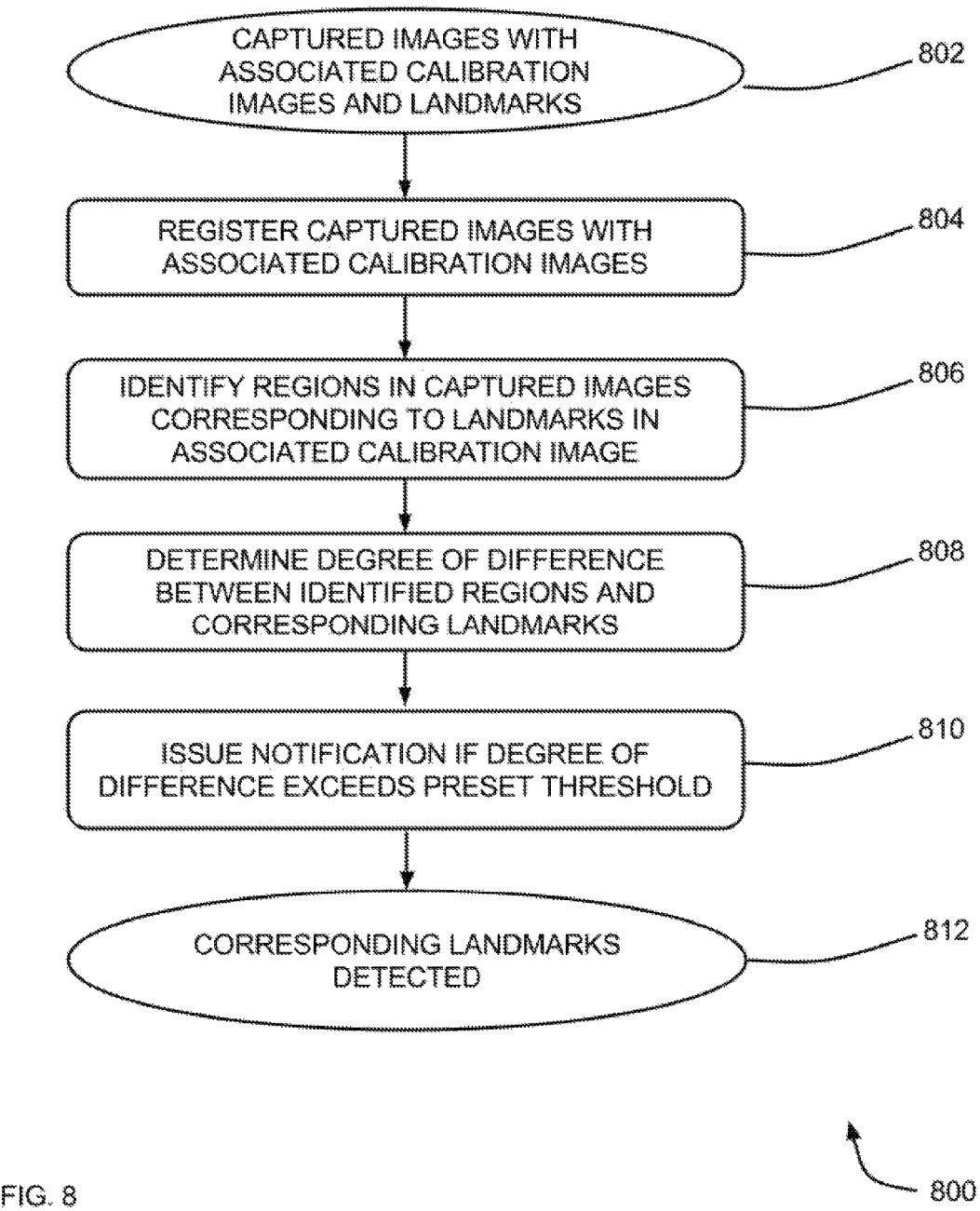
FIG. 8 is a flowchart of a method to track changes in an ocular scene by detecting landmarks in captured images received from an imaging instrument corresponding to landmarks in associated calibration images, received from a different imaging instrument, and issuing a notification if the degree of difference between the corresponding landmarks exceeds a preset threshold.

FIG. 8 is a flowchart of method 800 to detect landmarks in a set of captured images. Method 800 solves the need in the art to detect changes in landmarks on a captured image relative to a corresponding landmark on a calibration image.

Method 800 includes a set of captured images with associated calibration images and landmarks on each calibration image 802, registering each captured image with the associated calibration image 804, identifying regions in the captured image that correspond to each landmark in the associated calibration image 806, determining a degree of difference between the detected landmark and the corresponding landmark in the associated calibration image 808, issuing a notification when the degree of difference between any detected landmark and corresponding landmark in the associated calibration image exceeds a preset threshold 810, resulting in the detection of corresponding landmarks.

In some aspects, detecting landmarks on each captured image includes determining a modified landmark associated with each landmark in the associated calibration image, and further includes determining a degree of difference between the detected landmark and the modified landmark associated with the corresponding landmark in the associated calibration image. In other aspects, a notification is issued when the degree of difference exceeds a preset threshold. In other aspects, the modified landmark associated with each landmark in the associated calibration image is determined based on the time elapsed since the calibration image was captured. In yet other aspects, the modified landmark associated with each landmark in the associated calibration image is determined based on a set of factors including the age or health of a patient whose ocular scene is being imaged, the type of pathology found in the ocular scene, or other medical conditions associated with the patient whose ocular scene is being imaged. In yet other aspects, the set of factors is selected by a physician.

Conclusion

A system to track changes in an ocular scene relative to a set of calibration images is described. Although specific aspects are illustrated and described herein, it will be appreciated by those of ordinary skill in the art that any arrangement which is calculated to achieve the same purpose may be substituted for the specific aspects shown. This application is intended to cover any adaptations or variations. For example, although described in terms of light source and imaging system, one of ordinary skill in the art will appreciate that implementations can be made using any other system capable of constructing an image of an ocular scene. Additionally, although described in terms of landmarks on the calibration images, one of ordinary skill in the art will appreciate that implementations can also be made wherein regions of interest to be tracked are identified by other means such as through computer aided diagnosis, or expert systems. Further, also described in terms of a first instrument and a second instrument, one of ordinary skill in the art will appreciated that more or fewer instruments may be used to image the ocular scene and generate calibration and captured images.

In particular, one of skill in the art will readily appreciate that the names of the methods and apparatus are not intended to limit aspects. Furthermore, additional methods and apparatus can be added to the components, functions can be rearranged among the components, and new components to correspond to future enhancements and physical devices used in aspects can be introduced without departing from the scope of aspects. One of skill in the art will readily recognize that aspects are applicable to future types of landmarks that may be identified on calibration images, derived or interpreted, different methods of imaging and ocular scene, and new algorithms to associate captured images with calibration images, and new algorithms to detect landmarks in captured images corresponding to landmarks on calibration images.

The terminology used in this application is meant to include all systems to track changes in an ocular scene relative to a set of calibration images and landmarks on the calibration images, and alternate technologies which provide the same functionality as described herein.

What is claimed:

1. An imaging instrument comprising:
an eyepiece;
a light source operable to project light through the eyepiece;
an imaging system operable to image an ocular scene through the eyepiece; and
a processing system operable to receive a set of one or more calibration images, and further operable to capture an image of the imaged ocular scene associated with a calibration image in the set of calibration images.

2. The imaging system of claim 1 comprising:
a sensor operable to image the ocular scene and further operable to transfer the imaged ocular scene to the processing system; and
a lens system situated between the sensor and the ocular scene, operable to focus and magnify the imaged ocular scene onto the sensor based on a focus parameter and a magnification parameter.

3. The imaging system of claim 2 wherein the lens system comprises:
a first lens;
a second lens situated between the first lens and the sensor; and
a mechanism operable to vary the distance between the first lens and second lens, and further operable to vary the distance between the second lens and the sensor based on the focus parameter and the magnification parameter.

4. The imaging system of claim 3 wherein the mechanism comprises:
a motorized system operable to vary the distance between the first lens and second lens.

5. The imaging instrument of claim 2 further comprising:
a positioning system operable to rigidly change the orientation of the imaging and lens systems relative to the eyepiece based on an orientation parameter.

6. The imaging instrument of claim 5 wherein the processing system further comprises:
a control system operable to set the values of the focus parameter and the magnification parameter of the lens system based on the set of calibration images and the imaged ocular scene, and further operable to set the value of the orientation parameter of the positioning system based on the set of calibration images and the imaged ocular scene.

7. The imaging instrument of claim 1 wherein the processing system further comprises:
a transceiver operable to transmit a set of captured images to a mobile device.

8. The imaging instrument of claim 7 wherein the mobile device is one from the set of a smartwatch, a mobile phone, a mobile tablet, a laptop, a desktop computer, and a server.

9. A system for imaging an ocular scene comprising:
a set of machine readable instructions embodied in a non-transitory medium operable to receive a set of calibration images, further operable to receive a set of landmarks on each of the calibration images, and further operable to receive a set of captured images of an ocular scene from an imaging instrument, wherein each captured image is associated with a calibration image in the set of calibration images, and further operable to detect landmarks on each of the captured images wherein each detected landmark corresponds to a landmark in the set of landmarks on the associated calibration image.

10. The system of claim 9 wherein the machine readable instructions further comprise:
a second set of machine readable instructions embodied in a non-transitory medium operable to determine the degree of change between the detected landmarks and the corresponding landmarks on the associated calibration images, and further operable to display a notification if the degree of change exceeds a preset threshold.

11. The system of claim 9 wherein the machine readable instructions further comprise:
a second set of machine readable instructions embodied in a non-transitory medium operable to determine a modified landmark associated with each landmark on each calibration image; and
a third set of machine readable instructions embodied in a non-transitory medium operable to determine the degree of change between the detected landmarks and the modified landmarks associated with the corresponding landmarks on the associated calibration images, and further operable to display a notification if the degree of change exceeds a preset threshold.

12. The system of claim 9 wherein the second set of machine readable instructions further comprises:
a fourth set of machine readable instructions embodied in a non-transitory medium operable to determine a modified landmark associated with each landmark on each calibration image based on a user selected change trajectory.

13. A method to track changes in an ocular scene comprising:
receiving a set of calibration images;
receiving a set of landmarks on each calibration image;
capturing a set of images of an ocular scene;
associating each captured image with a calibration image in the set of calibration images; and
detecting landmarks on each captured image wherein each detected landmark corresponds to a landmark on the associated calibration image.

14. The method of claim 13 wherein capturing a set of images further comprises:
illuminating the ocular scene; and
imaging the ocular scene.

15. The method of claim 14 wherein imaging the ocular scene further comprises:
determining a focus parameter, a magnification parameter, and an orientation parameter based on the imaged ocular scene and the set of calibration images; and
imaging the ocular scene using the determined focus parameter, the determined magnification parameter and the determined orientation parameter.

16. The method of claim 15 wherein detecting landmarks on each captured image further comprises:
registering the captured image with the associated calibration image; and
identifying regions in the captured image that correspond to each landmark in the associated calibration image.

17. The method of claim 16 wherein detecting landmarks on each captured image further comprises:
determining a degree of difference between the detected landmark and the corresponding landmark in the associated calibration image.

18. The method of claim 17 further comprising:
issuing a notification when the degree of difference between any detected landmark and corresponding landmark in the associated calibration image exceeds a preset threshold.

19. The method of claim 18 wherein detecting landmarks on each captured image further comprises:
determining a modified landmark associated with each landmark in the associated calibration image; and
determining a degree of difference between the detected landmark and the modified landmark associated with the corresponding landmark in the associated calibration image.

20. The method of claim 19 further comprising:
issuing a notification when the degree of difference between any detected landmark and modified landmark associated with the corresponding landmark in the associated calibration image exceeds a preset threshold.

* * * * *